(12) United States Patent
Awaad et al.

(10) Patent No.: US 8,933,267 B2
(45) Date of Patent: Jan. 13, 2015

(54) **COMPOUNDS FOR USE AS ANTI-ULCER AGENT AND/OR ANTI-*HELICOBACTER PYLORI* AGENT AND PHARMACEUTICAL COMPOSITIONS THEREOF**

(71) Applicant: King Saud University, Riyadh (SA)

(72) Inventors: Amani S. Awaad, Riyadh (SA); Reham Moustafa El-Meligy, Riyadh (SA); Ahmed M. Alafeefy, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 14/207,723

(22) Filed: Mar. 13, 2014

(65) Prior Publication Data

US 2014/0329778 A1    Nov. 6, 2014

(30) Foreign Application Priority Data

May 6, 2013  (EP) .................................... 13166649

(51) Int. Cl.
*C07C 311/46*  (2006.01)
*C07C 311/37*  (2006.01)
*A61K 31/195*  (2006.01)

(52) U.S. Cl.
CPC .................................... *C07C 311/46* (2013.01)
USPC ........... 562/431; 562/430; 514/562; 514/563; 514/564

(58) Field of Classification Search
CPC ... C07C 311/37; C07C 311/46; A41K 31/195
USPC .................... 562/430, 431; 514/562, 563, 564
See application file for complete search history.

(56) References Cited

U.S. PATENT DOCUMENTS 5,637,592 A   6/1997  Heeres et al.

FOREIGN PATENT DOCUMENTS

CA   2372731  *  8/2003
GB   2163747     3/1986

OTHER PUBLICATIONS

Scozzafava A. et al.: "Carbonic Anhydrase Inhibitors. A General Approach for the Preparation of Water-Soluble Sulfonamides Incorporating Polyamino-Polycarboxylate Tails and of Their Metal Complexes Possessing Long-Lasting, Topical Intraocular Pressure-Lowering Properties", Journal of Medicinal Chemistry, American Chemical Society, vol. 45, No. 7, 28 Mar. 2002, pp. 1466-1476.
European Search Report for corresponding Application No. EP 13166649.7 dated Sep. 16, 2013.

* cited by examiner

*Primary Examiner* — Shailendra Kumar
(74) *Attorney, Agent, or Firm* — Renner, Otto, Boisselle & Sklar, LLP

(57) ABSTRACT

The present invention relates to a compound according to formula I

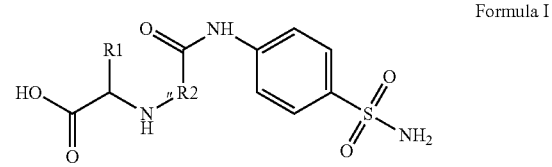

Formula I in particular as anti-ulcer agent and/or anti-*Helicobacter pylori* agent, wherein $R_1$ is selected from linear or branched $C_1$-$C_6$ alkyl, H, thioether and benzyl, and $R_2$ is selected from linear or branched $C_1$-$C_{10}$ alkanediyl and pharmaceutical compositions thereof.

14 Claims, No Drawings

COMPOUNDS FOR USE AS ANTI-ULCER AGENT AND/OR ANTI-*HELICOBACTER PYLORI* AGENT AND PHARMACEUTICAL COMPOSITIONS THEREOF

CROSS-REFERENCE TO RELATED APPLICATIONS

The present application is related to and claims priority under 35 U.S.C. §119(a) to pending European Application No. 13166649.7 filed 6 May 2013, the entirety of which is hereby incorporated by reference.

TECHNICAL FIELD

The present invention relates to compounds for use as anti-ulcer agent and/or anti-*Helicobacter pylori* agent and pharmaceutical compositions thereof.

BACKGROUND

Peptic ulcer (PU) is a major health problem which concerns the medical community all over the world. It is known that the major causative factor of a number of gastric pathologies including gastritis, peptic ulcers and certain gastric cancers is the *Helicobacter pylori* (*H. pylori*), a spiral microaerophilic S-shaped Gram negative bacterium which colonizes the gastric mucosa. Inflammation, injury and infection with *H. pylori* are the main causative factors. In spite of the substantial progress in many aspects of basic and clinical research, no clear, safe remedy is available (Newman, D. J.; Cragg. M.; Snader, K. M. (2003). Natural products as sources of new drugs over the period 1981-2002. *J. Nat. Prod.*, 66, 1022-1037; Chimenti F., Bizzarri B., Bolasco A., Secci D., Chimenti P., Carradori S., Granese A., Rivanera D., Lilli D., Zicari A., Scaltritod M. and Sisto F. (2007). A novel class of selective anti-*Helicobacter pylori* agents 2-oxo-2H-chromene-3-carboxamide derivatives. Bioorganic & Medicinal Chemistry Letters, 17: 3065-3071; Newman, D. J. (2008). Natural products as leads to potential drugs: An old process or the new hope for drug discovery. *J. Med. Chem.*; 51:2589-2599).

Sulphonamide derivatives showed many biological activities; early and recent researchers have suggested that sulfonamides are useful for the treatment of some staphylococci infections, especially against urinary infections. It was reported that they showed the highest inhibitory effect on gram positive bacteria, i.e. *Staphylococcus aureus, Nocardia asteroides, N. farcinia* and *Bacillus subtilis*. However, sulphonamide derivatives were also reported in treatment of Chagas disease, they showed in-vitro activity against two strains of *Trypanosoma cruzi*.

Furthermore, sulphonamide derivatives were used as hypoglycemic agent. Sulfonamide derivatives have several clinical applications against inflammatory bowel syndrome and other related ailments in addition to their tendency to accumulate in hypoxic tumours.

Sulfa drugs are well known inhibitors of dihydrofolate reductase. Moreover, several literatures reviews mentioned their ability to selectively inhibit the different carbonic anhydrase isoforms. Recently, some new sulfonamide derivatives with remarkable antitumor activity were prepared in laboratory ($IC_{50}$ 2.5-5.5 µg/mL).

The objective problem to be solved by the present invention is, therefore, to provide novel anti-ulcer and/or anti-*Helicobacter pylori* agents having improved effectivity and safety properties as well as low toxicity.

SUMMARY

This object has been solved by a compound according to formula I,

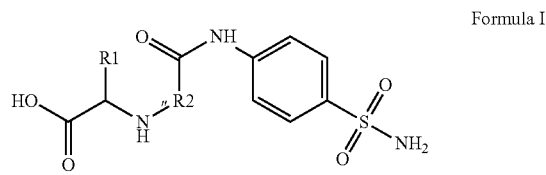

wherein $R_1$ is selected from linear or branched $C_1$-$C_6$ alkyl, H, thioether and benzyl; and $R_2$ is selected from linear or branched $C_1$-$C_{10}$ alkanediyl.

The term alkanediyl refers to saturated hydrocarbon groups bound by two different carbon atoms to the respective substituents.

Preferably, $R_1$ is selected from iso-butyl, methyl, iso-propyl, sec-butyl, H, 2-methylmercapto ethyl or benzyl.

Iso-butyl group is a group having the formula —$CH_2$—$CH(CH_3)_2$. Iso-propyl represents a group having the formula —$CH(CH_3)_2$. Sec-butyl represents a group having the formula —$CH(CH_3)(C_2H_5)$. 2-Methylmercapto ethyl represents a group having the formula —$C_2H_5SCH_3$.

Preferably, $R_2$ is iso-butyl.

More preferably, $R_2$ is selected from linear or branched $C_1$ to $C_5$ alkandiyl.

Most preferably, $R_2$ is methylene.

The problem has also been solved by the inventive compound of formula I for use as anti-ulcer agent and/or anti-*Helicobacter pylori* agent.

The problem has further been solved by a pharmaceutical composition comprising an inventive compound of formula I.

Finally, the problem has been solved by the inventive pharmaceutical composition for use as anti-ulcer agent and/or anti-*Helicobacter pylori* agent.

Surprisingly, it was found that the inventive compounds feature high anti-ulcer and anti-*Helicobacter pylori* activity by featuring significantly lowered toxicity at the same time.

DETAILED DESCRIPTION

The term "pharmaceutical composition", as used herein, is intended to comprise one or more of the compounds represented by the general formula I as defined above.

The pharmaceutical composition can be, for example, in a liquid form, e.g. a solution, syrup, elixier, emulsion and suspension, or in a solid form, e.g. a capsule, cablet, tablet, pill, powder and suppository. Granules or semi-solid forms and gel caps are also considered. In case that the pharmaceutical composition is a liquid or a powder, dosage unit optionally is to be measured, e.g. in the dosage unit of a teaspoonful. In addition to the compound, the pharmaceutical composition can comprise, for example, flavouring agents, sweeteners, dyes, stabilizers, colouring agents, diluents, suspending agents, granulating agents, lubricants, binders and disintegrating agents. A tablet, for example, can be coated. All of the formulations mentioned can be intended for immediate-release, timed-release and sustained release.

All components of the pharmaceutical composition have to be pharmaceutically acceptable. The term "pharmaceutically acceptable" means at least non-toxic. The therapeutically active compounds should preferably be present in the above-mentioned pharmaceutical composition in a concentration of about 0.1 to 99.5, preferably of about 0.5 to 95% by weight of the total mixture.

It will be understood by those skilled in the art that various modifications and substituents may be made to the invention as described above without departing from the spirit and scope of the invention. Accordingly, it is understood that the present invention have been described by way of illustration and not limitation.

EXPERIMENTAL

Example 1

Synthesis

4-Methyl-2-[2-oxo-2-(4-sulfamoylphenylamino) ethylamino]pentanoic acid

2-Chloroacetyl chloride (1.12 g, 0.01 mol) (2) was added dropwise with vigorous stirring to a cold suspension of sulfanilamide (1.72 g, 0.01 mol) (1) in 10 ml dichloromethane containing 2 drops triethylamine. Stirring was continued for 1 hour and the separated solid was filtered, washed with ether, dried and crystallized from aqueous-ethanol.

Yield, 69%; M.P. 270-272° C.; $^1$H NMR (DMSOd$_6$): δ 0.90 (d, 6H, J=12.0 Hz, 2CH$_3$), 1.49 (m, 1H, CH), 1.80 (t, 2H, J=9.0 Hz, CH$_2$), 2.51 (s, 1H, NH, D$_2$O exchange.), 3.26 (s, 2H, CH$_2$), 3.49 (t, 1H, J=8.5 Hz, CH), 4.21 (s, 2H, NH$_2$, D$_2$O exchange.), 7.30 (s, 1H, NH, D$_2$O exchange.), 7.60 (d, 2H, J=7.5 Hz, Ar—H), 7.79 (d, 2H, J=7.67 Hz, Ar—H), 10.55 (s, 1H, OH, D$_2$O exchange). $^{13}$C NMR: δ 22.6 (2CH$_3$), 24.3 (CH), 41.1 (CH$_2$), 50.2 (CH$_2$), 59.4 (CH), 118.6, 126.7, 138.4, 141.4 (Ar—C), 169.0, 174.7 (2C=O). MS (EI): m/z 343 [M$^+$, %]. Anal. (C$_{14}$H$_{21}$N$_3$O$_5$S) C, H, N.

The obtained alkyl halide (3) was then refluxed with leucine (4) in alcohol containing anhydrous potassium carbonate in the presence of catalytic amount of potassium iodide. The product (5) was obtained in about 50% yield and purified by column chromatography. The structure was confirmed by NMR spectra. The spectrum showed the aliphatic protons at δ of 0.9 ppm, two different protons on two different tertiary carbons δ at 1.49 and 3.49 and the carbons bearing them at 22.6, 24.3 and 59.9 respectively. Two CH$_2$ groups at δ 1.80, 3.26 and their carbons appeared at 41.1, 50.2, respectively. The SO$_2$NH$_2$ protons were found at δ 4.21. Two singlets corresponding to two NH groups were seen at δ 2.51 and 7.30, respectively. One OH appeared at δ 10.55 due to the free carboxyl group of leucine. The two carbonyl groups were seen at δ 169.0 and 174.7. The two dimensional spectrum showed that the obtained structure is in accordance with the proposed one.

The compound was identified as; 4-Methyl-2-[2-oxo-2-(4-sulfamoylphenylamino)ethylamino]pentanoic acid (5).

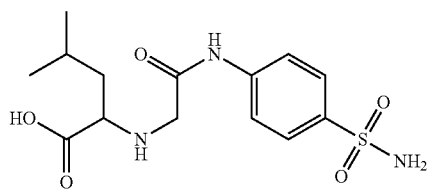

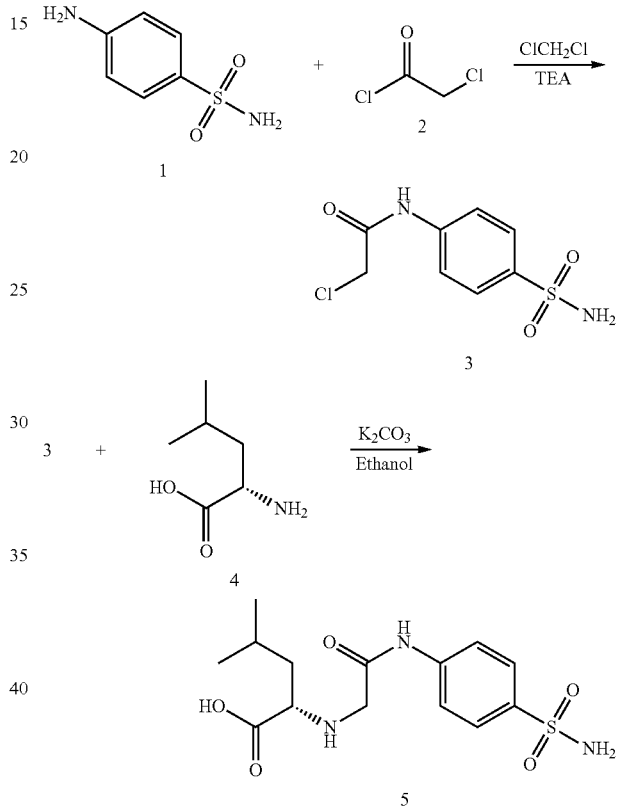

Scheme

Example 2

Biological Activity

Animals

Swiss albino mice of both sex (26-30 g) and male Wistar rats (180-200 g) were purchased from the animal house of King Saud University, KSA. Animals were housed in standard polypropylene cages with wire mesh top and maintained under standard conditions (temperature 23±1.0° C., humidity 55±10%, 12 h light/12 h dark cycle). They fed with a standard pellet diet with water ad libitum and were allowed to adapt to the laboratory environment for one week before experimentation.

Determination of Median Lethal Dose (LD$_{50}$):

The oral median lethal dose (LD$_{50}$) of the target compound was determined as described by (Lorke D. (1983). A new approach to practical acute toxicity testing. *Arch Toxicology*, 54, 251-287). Swiss albino mice in groups of six, received one of 50, 100, 500, or 1000 mg/kg doses of the target compound.

Control animals were received the vehicle and kept under the same conditions. Signs of acute toxicity and number of deaths per dose within 24 h were recorded.

The target compounds in doses up to 1000 mg/kg did not produce any behavioral changes and mortality in mice. Therefore, it can be categorized as highly safe since substances possessing $LD_{50}$ higher than 50 mg/kg are nontoxic (Soliman G. A., Donia A. M., Awaad A. S., Alqasoumi S. I., and Yusufoglu H. Effect of Emex spinosa, Leptadenia pyrotechnica, Haloxylon salicornicum and Ochradenus baccatus extracts on the reproductive organs of adult male rats. Pharmaceutical Biology, 50(1): 105-112).

Antiulcerogenic Activity:

Evaluation of the anti-ulcerogenic activity was carried out using absolute ethanol-induced ulcer model (Bighettia A. E., Antonio M. A., Kohna L. K., Rehdera V. L. G., Foglioa M. A., Possentia A., Vilelaa L., Carvalho J. E. (2005). Antiulcerogenic activity of a crude hydroalcoholic extract and coumarin isolated from *Mikania laevigata* Schultz Bip. *Phytomedicine*, 12, 72-77). Thirty male Wistar rats were divided into 5 groups each of 6 rats. Group 1 received the vehicle and served as control, group 2 received ranitidine (100 mg/kg) and served as standard, groups 3, 4 and 5 received the synthesized compound at doses 25, 50 and 100 mg/kg respectively.

Rats of all groups were fasted for 24 h then all medications were administered orally. One hour after treatment, the animals received an oral dose of absolute ethanol (1 ml/200 g) and then sacrificed one hour later, by ether inhalation, the stomachs were rapidly removed, opened along their greater curvature and gently rinsed under running tap water.

Number of lesions in the glandular part of the stomach were measured under an illuminated magnifying microscope (10×). Long lesions were counted and their lengths were measured. Petechial lesions were counted, and then each five petechial lesions were taken as 1 mm of ulcer.

The lesion scores: The mucosal lesions were quantified by the scoring system (0-5) 0=no damage, 1=Local edema and inflammation without ulcers; 2=One ulcer without inflammation; 3=one to two ulcers with inflammation & lesion diameter <1 cm; 4=More than two ulcers with lesion diameter 1-2 cm; 5=Sever ulceration with lesion diameter >2 cm (Morris et al., 1989).

Ulcer index: To calculate the ulcer index (mm), the sum of the total length of long ulcers and petechial lesions in each group of rats was divided by its number. The curative ratio was determined according to the formula:

% Protection of control ulcer=Control UI−Test UI/Control UI×100

The present result of anti-ulcerogenic activity showed that the amino acid-sulfanilamide hybrid possessed a potent dose dependent anti-ulcerogenic activity. It produced percent protection of control ulcer ranged from 16.7% to 66.7%, while the standard drug ranitidine (100 mg/kg) produced 45.05% (Table 1). The target compound (Compound 5) (100 mg/kg) was significantly more effective than the standard in reducing ulcer index and ulcer score.

TABLE 1

Anti-ulcerogenic effect of amino acid-sulfanilamide compound on absolute alcohol-induced ulcer in rats.

| Groups | Dose mg/kg | score | no of ulcers | ulcer index | % protection |
|---|---|---|---|---|---|
| Control | — | 3.25 | 16.40 ± 0.5 | 10.92 ± 1.74 | 0 |
| Ranitidine | 100 | 2.2 | 6.9*** ± 1.05 | 6.0* ± 1.24 | 45.05 |
| Compound 5 | 25 | 2.2 | 11.1* ± 1.79 | 9.1** ± 1.24 | 16.7 |
| Compound 5 | 50 | 1.6 | 8** ± 1.58 | 4.48** ± 1.08 | 59 |
| Compound 5 | 100 | 1.4 | 6.2*** ± 1.3 | 3.64*** ± 0.47 | 66.7 |

Data are expressed as mean ± SD, n = 6, *p ≤ 0.05, p ≤ 0.01, *p ≤ 0.001

Effect on Liver and Kidney Functions:

Male Wister rats were divided into 2 equal groups each of 10 rats. The 1st group was left as a control and administrated the vehicle orally, while the 2nd group was orally administrated the synthesized compound in a dose of 100 mg/kg for 15 days. After the examination period, 6 hr after the last dose blood samples were collected from the orbital plexus of rats. Samples were left to clot at room temperature for 30 min then centrifuged at 1000 rpm for 20 min.

The collected sera were used for determination of the activity of both (AST) aspirate aminotransferase and (ALT) alanine aminotransferase as liver markers. In addition, levels of blood urea, serum creatinine were also estimated as kidney markers (Awaad A. S., Al-Jaber N. A., Moses J. E., El-Meligy R. M. and Zain M. E. (2013). Antiulcerogenic Activities of the Extracts and Isolated Flavonoids of *Euphorbia cuneata* Vahl. *Phytother. Res.* 27: 126-130).

Both liver and kidney functions were not affected as there is no significant difference between control and test group in all experiments, at the 0.05 level of probability (Table 2). These results showed that, the compound didn't reveal hepatotoxic manifestation. In addition, no apparent nephrotoxic manifestations were recorded.

TABLE 2

Effect of amino acid-sulfanilamide compound on liver and kidney functions of rats.

| Groups | ALT (U/l) | AST (U/l) | Blood Urea (mg/dl) | Creatinine (mg/dl) |
|---|---|---|---|---|
| Control | 42.49 ± 0.37 | 60.77 ± 0.37 | 70.50 ± 1.36 | 0.88 ± 0.02 |
| Compound 5 (100 mg/kg) | 38.67 ± 0.22 | 63.23 ± 0.39 | 65.50 ± 1.9 | 0.85 ± 0.02 |

Data are expressed as mean ± SD, n = 10

In-Vitro Anti-*Helicobacter pylori* Activity
Bacterial Isolates

A total of seven clinical isolates of *H. pylori* were isolated from 19 biopsies received from patients diagnosed with gastritis or peptic ulcer disease at Al-Kasr Al-Ainy hospital, Cairo, Egypt. Clinical isolates were symbolized from KA1 to KA7. Isolates were grown in *Brucella* agar plates (Difco, Detroit, Mich., USA) containing 10% v/v sheep serum at 37° C.

Identification was carried out using Gram stain and catalase, oxidase and urea hydrolysis activities. *Helicobacter pylori* ATCC 43504 was used as control.

Determination of Anti-*Helicobacter pylori* Activity

Determination of the amino acid-sulfanilamide hybrid activity against *H. pylori* was carried out using disk diffusion method (McNulty C, Owen R., Tompkins D., Hawtin P., McColl K., Price A., Smith G. and Teare L. (2002). *Helicobacter pylori* susceptibility testing by disc diffusion. *Journal of Antimicrobial Chemotherapy*, 49: 601-609). The amino acid-sulfanilamide hybrid compound was dissolved in 2% Tween (v/v), in order to obtain final concentration of 2 mg/ml.

Sterile 6 mm disks utilized were imbibed in 1 mL of compound solution and were deposited on the surface of the plate of Mueller-Hinton agar with 10% sheep blood inoculated with *H. pylori*, in a suspension of $6 \times 10^8$ CFU/mL (McFarland turbidity standard 2), using amoxicillin (30 µg) and erythromycin (15 µg) as the standard antibiotics. The plate was incubated at 37° C. under microaerophilic conditions in an atmosphere of 5-15% $O_2$ and 5-10% $CO_2$ for 48-72 h.

Determination of the Minimum Inhibitory Concentration (MIC)

The Minimum inhibitory concentration (MIC) was carried out by the broth microdilution assay (EUCAST, 2003). A total of 100 µL of BHI broth supplemented with 10% defibrinated sheep blood inoculated with $6 \times 10^8$ *H. pylori* (McFarland turbidity standard 2) and 100 µL A of serial dilutions of amino acid-sulfanilamide hybrid compound dissolved in 2% Tween (v/v) was added to each well in the microplate, to reach final concentrations of 12.5; 25; 50; 100; 200; 400 and 800 µg/ml. The microplate was incubated at 37° C. under microaerophilic conditions in an atmosphere of 5-15% $O_2$ and 5-10% $CO_2$, for 48-72 h. After incubation, the plates were visually examined, the optical density was determined at 450 nm and each well was replicated in blood agar (Mueller-Hinton agar with 5% sheep blood), to determine the MIC.

The activity of amino acid-sulfanilamide hybrid compound (Compound 5) against *H. pylori* was determined (Table 3). Seven isolates of *H. pylori* were obtained from 19 gastric biopsies and their susceptibility to two antibiotics and amino acid-Sulfanilamide hybrid compound was determined by disc diffusion (Table 3). All the isolates of *H. pylori* were sensitive to amino acid-Sulfanilamide hybrid compound, amoxicillin and erythromycin.

The results revealed that the highest inhibition zones, 19, 18 and 17 mm, were obtained against *H. pylori* KA7, KA1 and KA6, respectively. On the other hand, the lowest inhibition zone 15 mm was obtained against *H. pylori* KA2, KA4 and KA5 (Table 3).

TABLE 3

Activity of amino acid-sulfanilamide hybrid compound and two antibiotics against clinical isolates of *H. pylori*.

| | Inhibition zone (mm) | | |
|---|---|---|---|
| *H. pylori* strains | Compound 5 (2 mg) | Amoxicillin (30 µg) | Erythromycin (15 µg) |
| KA1 | 18 | 22 | 21 |
| KA2 | 15 | 23 | 22 |
| KA3 | 16 | 24 | 24 |
| KA4 | 15 | 23 | 23 |
| KA5 | 15 | 25 | 21 |
| KA6 | 17 | 26 | 25 |
| KA7 | 19 | 27 | 24 |
| ATCC 43504 | 16 | 33 | 29 |

The minimum inhibitory concentration (MIC) was determined for the amino acid-sulfanilamide hybrid compound using broth dilution method (Table 4). The results showed that the lowest minimum inhibitory concentrations (12.5 and 25 µg/mg) were obtained against *H. pylori* KA7 and KA6, respectively (Table 4).

TABLE 4

Minimum inhibitory concentration (MIC) of amino acid-sulfanilamide hybrid compound (Compound 5) against clinical isolates of *H. pylori*.

| *H. pylori* strains | Concentration (µg/ml) |
|---|---|
| KA1 | 50 |
| KA2 | 50 |
| KA3 | 50 |
| KA4 | 50 |
| KA5 | 50 |
| KA6 | 25 |
| KA7 | 12.5 |
| ATCC 43504 | 50 |

The features disclosed in the foregoing description and in the claims may both separately or in any combination thereof be material for realizing the invention in diverse forms thereof.

The invention claimed is:

1. Compound of formula I,

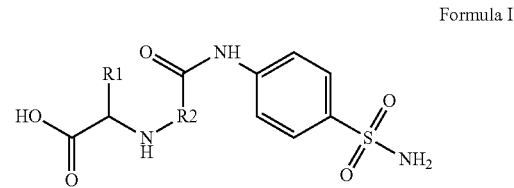

Formula I wherein $R_1$ is selected from linear or branched $C_1$-$C_6$ alkyl, thioether and benzyl; and $R_2$ is selected from linear or branched $C_1$-$C_{10}$ alkanediyl.

2. Compound of formula I according to claim 1, wherein $R_1$ is selected from iso-butyl, methyl, iso-propyl, sec-butyl, H, 2-methylmercapto ethyl or benzyl.

3. Compound of formula I according to claim 1, wherein $R_2$ is iso-butyl.

4. Compound of formula I according to claim 1, wherein $R_2$ is selected from linear or branched $C_1$ to $C_5$ alkanediyl.

5. Compound of formula I according to claim 1, wherein $R_2$ is methylene.

6. Method of treatment of an animal comprising administering a compound of formula I

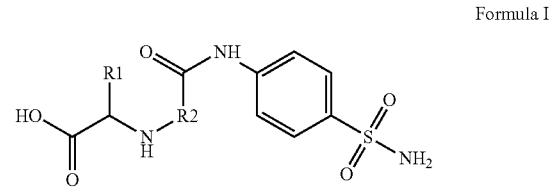

Formula I wherein $R_1$ is selected from linear or branched $C_1$-$C_6$ alkyl, H, thioether and benzyl; and $R_2$ is selected from linear or branched $C_1$-$C_{10}$ alkanediyl, as one or both of an anti-ulcer agent or an anti-*Helicobacter pylori* agent.

7. Pharmaceutical composition comprising a compound of formula I according to claim 1.

8. Method of treatment of an animal comprising administering a pharmaceutical composition comprising a compound of formula I

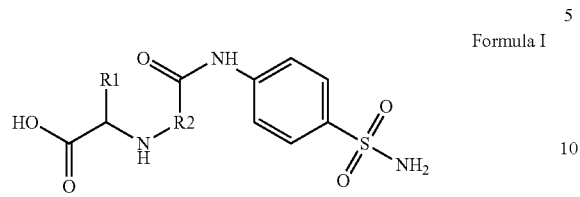

Formula I wherein $R_1$ is selected from linear or branched $C_1$-$C_6$ alkyl, H, thioether and benzyl; and $R_2$ is selected from linear or branched $C_1$-$C_{10}$ alkanediyl, as one or both of an anti-ulcer agent or an anti-*Helicobacter pylori* agent.

9. Compound of formula I according to claim 2, wherein $R_2$ is iso-butyl.

10. Compound of formula I according to claim 2, wherein $R_2$ is selected from linear or branched $C_1$ to $C_5$ alkanediyl.

11. Compound of formula I according to claim 3, wherein $R_2$ is selected from linear or branched $C_1$ to $C_5$ alkanediyl.

12. Compound of formula I according to claim 2, wherein $R_2$ is methylene.

13. Compound of formula I according to claim 3, wherein $R_2$ is methylene.

14. Compound of formula I according to claim 4, wherein $R_2$ is methylene.

* * * * *